(12) United States Patent
Bernard et al.

(10) Patent No.: US 8,569,358 B2
(45) Date of Patent: Oct. 29, 2013

(54) USE OF SILYMARIN AND/OR CONSTITUENTS THEREOF AS SKIN OR HAIR PIGMENTATION PROMOTERS

(75) Inventors: Philippe Bernard, Orleans (FR); Francois-Xavier Bernard, Saint Maurice la Clouere (FR)

(73) Assignees: GreenPharma, Saint Beauzire (FR); BioAlternatives, Gencay (FR)

( * ) Notice: Subject to any disclaimer, the term of this patent is extended or adjusted under 35 U.S.C. 154(b) by 1068 days.

(21) Appl. No.: 11/818,943

(22) Filed: Feb. 13, 2006

(65) Prior Publication Data

US 2008/0033037 A1 Feb. 7, 2008

(30) Foreign Application Priority Data

Feb. 11, 2005 (FR) ..................... 05 01446

(51) Int. Cl.
 *A01K 43/32* (2006.01)
 *A61K 31/335* (2006.01)

(52) U.S. Cl.
 USPC ........................................................ 514/452

(58) Field of Classification Search
 USPC ........................................................ 514/452
 See application file for complete search history.

(56) References Cited

U.S. PATENT DOCUMENTS

| | | | |
|---|---|---|---|
| 5,792,448 | A | 8/1998 | Dubief et al. |
| 6,399,046 | B1 | 6/2002 | Schonrock et al. |
| 6,409,996 | B1 | 6/2002 | Plaschke |
| 2002/0155074 | A1 | 10/2002 | Pinnell |
| 2005/0002962 | A1 | 1/2005 | Pasco et al. |

FOREIGN PATENT DOCUMENTS

| | | |
|---|---|---|
| DE | 43 23 614 A1 | 1/1995 |
| EP | 0 180 505 A1 | 5/1986 |
| EP | 0 180 505 B1 | 5/1986 |
| EP | 0 680 744 A1 | 11/1995 |
| EP | 0 680 744 B1 | 11/1995 |
| JP | A 05-140181 | 6/1993 |
| JP | A 06-065031 | 3/1994 |
| JP | A 07-112916 | 5/1995 |
| JP | A 07-304636 | 11/1995 |
| JP | A 2000-169328 | 6/2000 |
| JP | A 2000-169332 | 6/2000 |
| JP | A 2002-220333 | 8/2002 |
| JP | A 2003-171240 | 6/2003 |
| JP | A 2004-002264 | 1/2004 |
| JP | A 2004-026812 | 1/2004 |
| WO | WO 99/55326 A1 | 11/1999 |
| WO | WO 01/13879 A1 | 3/2001 |
| WO | WO 01/18125 A1 | 3/2001 |
| WO | WO 2004/014413 A1 | 2/2004 |
| WO | WO 2004/032890 A2 | 4/2004 |

OTHER PUBLICATIONS

Holzle (Pigmented lesions as a sign of photodamage, Br. J. Dermatol. 1992, vol. 127, Suppl. 41, pp. 48-50).*
Sheldon "Cutaneous photo-damage, oxidative stress and topical antioxidant protection", American Academy of Dermatology Inc, vol. 48, No. 1, Jan. 2003.*
Jimenez-Cervantes et al "Inhibition of melanogenesis in response to oxidative stress: Transient down-regulation of melanocyte differentiation markers and possible involvement of microphthalmia transcription factor" Journal of Cell Science, vol. 114, pp. 2335-2344, 2001.*
Lee, David Y. W. et al., "Molecular Structure and Stereochemistry of Silybin A, Silybin B, Isosilybin A, and Isosilybin B, Isolated from *Silybum marianum* (Milk Thistle)," J. Nat. Prod., vol. 66, p. 1171-1174 (2003).
Siegrist, Walter et al., "Radioreceptor Assay for α-MSH Using Mouse B16 Melanoma Cells," Journal of Receptor Research, vol. 8, p. 323-343 (1988).
Philpott, Michael P. et al., "Human Hair Growth in Vitro," Journal of Cell Science, vol. 97, p. 463-471 (1990).
Dhanalakshmi, Sivanandhan et al., "Silibinin Prevents Ultraviolet Radiation-Caused Skin Damages in SKH-1 Hairless Mice Via a Decrease in Thymine Dimer Positive Cells and an Up-regulation of p53-p21/Cip1 in Epidermis," Carcinogenesis, vol. 25, No. 8, p. 1459-1465 (2004).
R. Jackson, "Elderly and Sun-Affected Skin—Distinguishing Between Changes Caused by Aging and Changes Caused by Habitual Exposure of Sun", *Canadian Family Physician*, pp. 1236-1243, vol. 47, Jun. 2001.
J. Ortonne, "Dyspigmentation of Aged Skin", *European Journal of Dermatology*, pp. 168-169, vol. 11, No. 2, Mar.-Apr. 2001.
L. Daniel et al., "Comparing Alternative Methods of Measuring Skin Color and Damage", *Cancer Causes Control*, pp. 313-321, vol. 20, No. 3, Apr. 2009.
Nerya, et al., "Chalcones as potent tyrosinase inhibitors: the effect of hydroxyl positions and numbers," Phytochemistry, 65, pp. 1389-1395, May 19, 2004.
Blarzino, et al., Abstract, "Lipoxygenase/H2O2-catalyzed oxidation of dihdroxyindoles: synthesis of melanin pigments and study of their antioxidant properties," Free Radic Biol Med, 26 (3-4), pp. 446-453, Feb. 1999.
Funasaka, et al., Abstract, "The depigmenting effect of alpha-tocopheryl ferulate on human melanoma cells," Br J Dermatol, 141 (1), pp. 20-29, Jul. 1999.
Office Action issued Sep. 29, 2011 in Japanese Patent Application No. 2007-554603 with English translation.

* cited by examiner

*Primary Examiner* — Brandon Fetterolf
*Assistant Examiner* — Jean Cornet
(74) *Attorney, Agent, or Firm* — Oliff & Berridge, PLC

(57) ABSTRACT

Describe is a method of administering to a subject silymarin, or of the main constituents thereof alone or as a mixture, chosen from silybin (or 2,3-dihydro-3-(4-hydroxy-3-methoxyphenyl)-2-(hydroxymethyl)-6-(3, 5,7-trihydroxy-4-oxobenzopyran-2-yl)benzodioxine), isosilybin, silydianin, silychristin, silandrin, silymonin and taxifolin, isolated enantiomers thereof and also salts thereof.

8 Claims, 4 Drawing Sheets

OBJECTIVE x10

CONTROL

SILYBIN 0.001%

OBJECTIVE x20

CONTROL

SILYBIN 0.001%

CONTROL                     SILYBIN 0.001%

D0; OBJECTIVE x4

UNTREATED　　　　　　　　SILYBIN 0.001%

D7; OBJECTIVE x4

UNTREATED　　　　　　　　SILYBIN 0.001%

D7; OBJECTIVE x10

UNTREATED　　　　　　　　SILYBIN 0.001%

D7; OBJECTIVE x4

UNTREATED　　　　　　　　　SILYBIN 0.001%

D17; OBJECTIVE x4

UNTREATED　　　　　　　　　SILYBIN 0.001%

D17; OBJECTIVE x10

UNTREATED　　　　　　　　　SILYBIN 0.001%

USE OF SILYMARIN AND/OR CONSTITUENTS THEREOF AS SKIN OR HAIR PIGMENTATION PROMOTERS

BACKGROUND

The colour of human skin depends on many factors and especially on race and sex, but also on environmental factors (season, exposure to sunlight, etc.); it is mainly dependent on the nature and concentration of melanin produced by the melanocytes. Melanocytes are specialized cells that synthesize melanin, using particular organelles, the melanosomes. Certain individuals naturally or accidentally have more or less localized pigmentation defects, requiring palliative local treatments, or demand more general treatments, for stimulating natural pigmentation.

Pigmentation is a natural effective protection against the harmful effects of ultraviolet radiation and against light-induced ageing of the skin in general. Skin pigmentation is also a protection against the onset of skin cancers; for the same magnitude of exposure to sunlight, dark-skinned individuals and ethnic groups develop far fewer skin cancers than individuals with pale skin.

Similarly, the colour of body hair and head hair is due to melanin. At different periods in their life, especially during ageing, certain people develop gradual depigmentation of their head hair, with a reduction in or even the stoppage of the melanogenesis process in the melanocytes associated with the hair bulbs. It would be very advantageous to be able to propose preventive or curative treatments capable of maintaining the process of pigmentation of the hair or of stimulating melanogenesis and pigmentation of hair with a tendency towards greying.

Exposure to sunlight and UV radiation have harmful effects on the hair, not only on the hair stem (oxidation and bleaching), but also, and more destructively, on the hair bulb, which may lead to loss of the hair. The recovery or stimulation of hair follicle pigmentation is capable of limiting the loss of the hair or of stimulating its regrowth. The use of harmless pro-pigmenting substances, by topical or systemic application in compositions, and which show good efficacy, is most particularly sought in order to treat natural regional hypopigmentations (of genetic origin, leukodermias such as vitiligo, and ageing) or accidental regional hypopigmentations (post-lesional scars or fungal mycoses), and also the stress-related loss of hair pigmentation or loss in the course of ageing.

The use of harmless substances, by topical or systemic application in compositions, and which protect the hair, limit its loss and/or stimulate its regrowth, under normal conditions, stress conditions, conditions of exposure to sunlight and/or in the course of ageing, is also of major interest.

The mechanism of formation of skin pigmentation is complex and schematically involves the following main steps:

tyrosine→dopa→dopaquinone→dopachrome→melanin.

Melanin is stored in organites or melanosomes, and then transferred to the neighbouring keratinocytes.

Each of these steps is essential to pigmentation. Tyrosinase (monophenol dihydroxyl phenylalanine: oxygen oxidoreductase EC 1.14.18.1) is the first enzyme involved in this sequence of reactions. It especially catalyses the reaction for transformation of tyrosine to dopa (dihydroxyphenylalanine) by virtue of its hydroxylase activity, and the reaction for transformation of dopa to dopaquinone via its oxidase activity. This tyrosinase acts only when it is in the mature state, under the action of certain biological factors; signalling via specific receptors such as the melanocortin receptors (MCR) is involved for induction of the melanin synthesis process by the melanocytes, especially the receptor MC1R.

In the epidermis, the melanocyte is involved in the epidermal melanic unit, which comprises a melanocyte surrounded by about 36 neighbouring keratinocytes. All individuals, without distinction as to phototype, have approximately the same number of melanocytes for a given area of skin. The ethnic differences, in terms of pigmentation, are not due to the number of melanocytes, but to the properties of their melanosomes. The melanosomes are aggregated as complexes and are of small size. They are highly specialized organelles whose sole function is to produce melanin. Gradually, as melanin is synthesized in the melanosomes, they move from the perinuclear region to the extremity of the melanocytes' dendrites. Via phagocytosis, the extremity of the dendrites is captured by the keratinocytes, and the melanosomes are redistributed in the keratinocytes. The dendritic extensions of the melanocytes, and the phagocytic activity of the keratinocytes, thus play an essential role in the transfer of melanin. Melanosome transfer is a phagocytic phenomenon considered as standard, which involves receptors known as the "protease-activated receptor 2" (PAR-2).

Although the level of melanin varies from one population to another, the amount of tyrosinase does not vary significantly and the level of tyrosinase messenger RNA is identical in white or black skin. The variations in melanogenesis are thus due to variations either in tyrosinase activity or in the capacity of the keratinocytes to phagocytose the melanosomes. This indicates that the keratinocyte is a major player in pigmentation; 1) it is quantitatively the major representative of the melanic unit, and is also the agent that influences, via information molecules (cytokines and hormones), a large proportion of the melanogenic activity; 2) it is its capacity for phagocytosis, combined with an adequate presentation of the melanosomes, in a dense dendritic network, which allows optimum distribution of melanin in the epidermis and pigmentation.

A substance is recognized as being pro-pigmenting if it acts directly or indirectly on activation of the melanin synthesis process, and/or if it stimulates the melanosome phagocytosis capacity by the keratinocytes.

Substances such as α-melanotropin (α-melanocyte-stimulating hormone, α-MSH) and corticotropin (adrenocorticotropic hormone, ACTH) stimulate melanin proliferation and synthesis by the melanocytes, via binding to specific receptors, especially the receptor MC1-R.

Few natural inducers are currently available and used for natural melanic pigmentation of the skin or the hair.

SUMMARY

There is thus a need for a novel agent for promoting the pigmentation of and/or for pigmenting human skin, body hair and/or head hair with activity that is more effective than the known agents, and which has a reinforced action so as to be able to be used in low amount without any side effects on the skin.

There is also a need for a novel agent for protecting the hair, limiting its loss and/or stimulating its regrowth, under normal conditions, stress conditions, conditions of exposure to sunlight and/or in the course of ageing.

In this regard, the Applicants have demonstrated that silybin and the other constituents of silymarin and silybin derivatives and/or analogues show good pro-pigmenting activity, even at low concentration, without showing any cytotoxicity.

These constituents and/or derivatives also have the advantage of acting on several major components of the pigmentation mechanism.

They stimulate 1) melanin biosynthesis by the melanocytes, 2) the formation of a dense dendritic network in the melanocyte, and 3) the phagocytic activity of the keratinocytes, thus increasing both the amount of melanin produced and the efficiency of the transfer of the melanosomes to the neighbouring keratinocytes.

Moreover, as regards the hair, it has been demonstrated that, 4) the invention clearly stimulates pigmentation of the follicles (hair bulbs) and that 5) the invention limits the degeneration and increases the survival of the follicles.

Silymarin is a mixture of various flavonolignans derived from taxifolin (a 2,3-dihydroflavanol) and coniferyl alcohol.

This mixture consists mainly of silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), a benzodioxane found in two diastereoisomeric forms (7"R,8"R and 7"S,8"S), silybin and isosilybin or isolated enantiomers thereof. The other constituents of silymarin are silydianin, silychristin, silandrin, silymonin and taxifolin or isolated enantiomers thereof.

Semi-synthetic or synthetic derivatives may also be used. Pharmaceutically and/or cosmetically acceptable salts may be used. Examples of salts that will be mentioned include the sodium salts, the pentaacetates and the tribromides. Glycosyl derivatives, and natural or synthetic esters or ethers may also be used. Mention will be made, for example, of silymarin-n-methylglycamate, esters with hemisuccinic acid, or silymarin pentamethyl or trimethyl ether.

All these compounds are listed in Chemical Abstracts: mention will be made, for example, of silymarin indexed under Registry Numbers 39468-33-2, 65666-07-1, 144160-53-2, 104444-08-8, 104444-07-7, the sodium salt under RN 66-580-75-4, the N-methyl glycamate under RN 53026-30-5, the sodium hemisuccinate under RN 52691-96-0, the pentaacetate, 27900-74-9, the tribromide 27359-07-5, the pentamethyl ether 27359-05-3, and the trimethyl ether 27359-04-2.

Taxifolin or 2-(3,4-dihydroxyphenyl)-2,3-dihydro-3,5,7-trihydroxy-4H-1-benzopyran-4-one (2R,3R)-(9CI) is indexed under RN 480-18-2.

Silybin or 2-[(2R,3R)-2,3-dihydro-3-(4-hydroxy-3-methoxyphenyl)-2-(hydroxymethyl)-1,4-benzodioxin-6-yl]-2,3-dihydro-3,5,7-trihydroxy-4H-1-benzopyran-4-one, (2R,3R)-(9CI) is indexed under RN 25888-70-6.

Isosilybin or 2-[2,3-dihydro-2-(4-hydroxy-3-methoxyphenyl)-3-(hydroxymethyl)-1,4-benzodioxin-6-yl]-2,3-dihydro-3,5,7-trihydroxy-4H-1-benzopyran-4-one, (2R,3R)-(9CI) is indexed under RN 72581-71-6.

Silydianin or 4-[(2R,3R)-3,4-dihydro-3,5,7-trihydroxy-4-oxo-2H-1-benzopyran-2-yl]-2,3,3a,7a-tetra-hydro-7a-hydroxy-8-(4-hydroxy-3-methoxyphenyl)-3,6-methanobenzo-furan-7(6H)-one, (3R,3aR,6R,7aR,8R)-(9CI) is indexed under RN 29782-68-1.

Silychristin or 2-[(2R,3S)-2,3-dihydro-7-hydroxy-2-(4-hydroxy-3-methoxyphenyl)-3-(hydroxymethyl)-5-benzo-furanyl]-2,3-dihydro-3,5,7-trihydroxy-4H-1-benzopyran-4-one, (2R,3R)-(9CI) is indexed under RN 33889-69-9.

Silandrin or 2-[(2R,3R)-2,3-dihydro-2-(4-hydroxy-3-methoxyphenyl)-3-(hydroxymethyl)-1,4-benzodioxin-6-yl]-2,3-dihydro-5,7-dihydroxy-4H-1-benzopyran-4-one, (2S)-(9CI) is indexed under RN 70815-2-6.

Silymonin or 4-[(2S)-3,4-dihydro-5,7-dihydroxy-4-oxo-2H-1-benzopyran-2-yl]-2,3,3a,7a-tetrahydro-7a-hydroxy-8-(4-hydroxy-3-methoxyphenyl)-3,6-methanobenzo-furan-7(6H)-one, (3R,3aR,6R,7aR,8R)-(9CI) is indexed under RN 70815-31-5.

Most of the constituents of silymarin exist in the form of diastereoisomers and/or enantiomers. These isomers may be separated via techniques known to those skilled in the art, to be used in optically pure form as active agent in compositions according to the invention.

Mention will be made in this respect of the publication by David Y. W. Lee, J. Nat. Prod. 2003, 66, 1171-1174, which describes the separation of silybin and isosilybin isomers into silybin A, silybin B, isosilybin A and isosilybin B.

Silymarin is conventionally obtained by extraction, especially of St Mary thistle, the compounds mentioned above being the main compounds responsible for the therapeutic action of the plant.

One subject of the present invention is the cosmetic or dermatological use of at least one taxifolin-based compound of natural, semi-synthetic or synthetic origin.

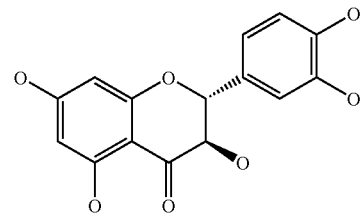

Structure of taxifolin

It may be an extract from plants containing this phytochemical family, for instance the genus *Silybum* (especially *Silybum marianum* (L.) Gaertn), of the Asteracea family. It may be silymarin or silibinin, a mixture of molecules initially isolated in the form of a mixture of adducts of a phenylpropanyl alcohol, coniferyl alcohol, with a 2,3-dihydroflavonol, taxifolin. This mixture consists mainly of silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), a benzodioxane found in two diastereoisomeric forms (7"R,8"R and 7"S,8"S). The other constituents of silymarin are silydianin, silychristin, silandrin, silymonin and taxifolin. All the glycosyl or non-glycosyl precursors of silybin, its isomers and its derivatives are of interest for the invention. Semi-synthetic or synthetic derivatives may also be used.

One subject of the present invention is the use for cosmetic and dermatological preparations of at least one source of flavonolignan in pure form or in the form of a mixture as a pigmenting and/or colouring agent for the skin and/or body hair and/or head hair.

DETAILED DESCRIPTION OF EMBODIMENTS

Figure 1:
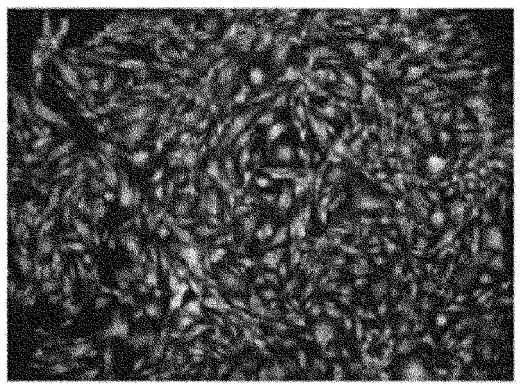
FIG. 1 shows fluorescence microscopy of normal human melanocytes labeled with CFDA (carboxyfluorescein succinimidyl ester diacetate).
Figure 1:
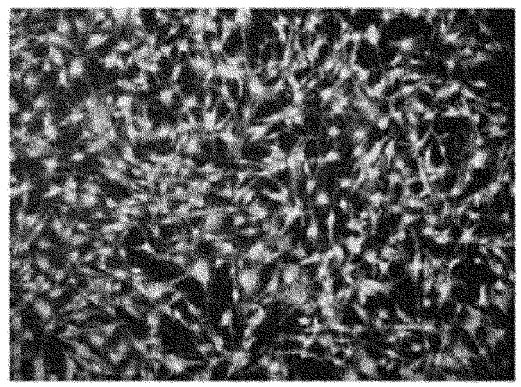
Figure 1:
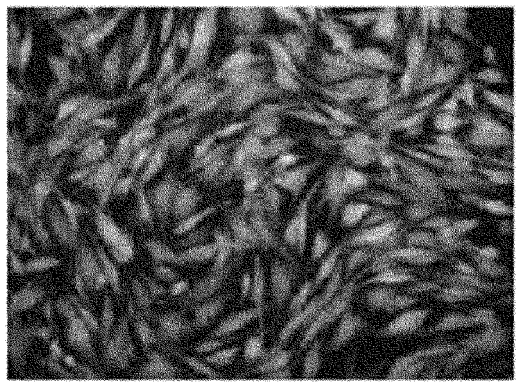
Figure 1:
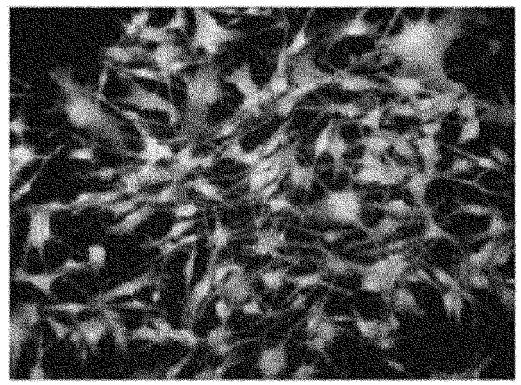

The present invention relates to the use of glycosyl or non-glycosyl flavonolignan derivatives of the silymarin family, or 3-hydroxyflavones, with silybin as prototype, but also silydianin, silychristin or isosilybin, in a composition, especially a cosmetic composition, the said derivatives and/or the said composition being intended to induce pigmentation of human skin, body hair or head hair.

The invention also relates to the use of flavonoglycan derivatives of the silymarin family, or 3-hydroxyflavones, with silybin as prototype, but also silydianin, silychristin or isosilybin, for the preparation of a composition, especially a dermatological composition, for inducing pigmentation of human skin, body hair or head hair.

The compounds may be identified as belonging to the family of flavonolignans of structure:

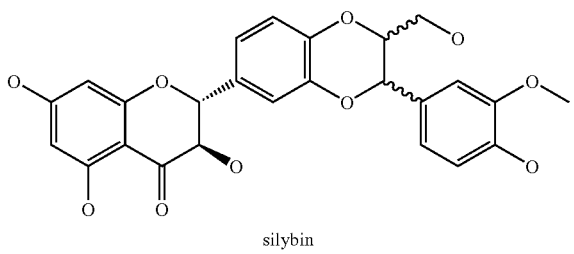 [SMILES: COc1cc(C2Oc3cc([C@H]4Oc5cc(O)cc(O)c5C(=O)[C@@H]4O)ccc3OC2CO)ccc1O]

silybin or more generally of structure (I):

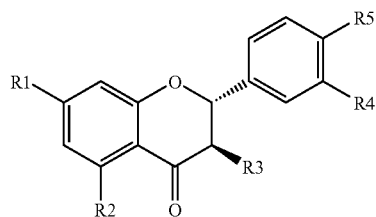

in which:
R1, R2, R3, R4 and R5, which may be identical or different, each represent
  either a hydrogen atom,
  or a halogen atom,
  or a nitro, $(C_1-C_6)$alkyl, $(C_1-C_6)$alkylCOOH, $(C_1-C_6)$alkylCOONa, trifluoro$(C_1-C_6)$alkyl, $(C_3-C_6)$cycloalkyl, acyl, $(C_2-C_6)$alkenyl, $(C_2-C_6)$alkynyl, $(C_6-C_{18})$aryl, $(C_6-C_{18})$arylCOOH, $(C_6-C_{18})$arylCOONa, $(C_6-C_{18})$aryl$(C_1-C_4)$alkyl, $(C_1-C_6)$alkyl$(C_6-C_{18})$aryl, $(C_5-C_{18})$heteroaryl containing from 1 to 3 heteroatoms, $CH(OH)(C_6-C_{18})$aryl, $CO(C_6-C_{18})$aryl, $(CH_2)_nCONH-(CH_2)_m-(C_6-C_{18})$aryl, $(CH_2)_nSO_2NH-(CH_2)_m-(C_6-C_{18})$aryl or $(CH_2)_nCONH-CH(COOH)-(CH_2)_p-(C_6-C_{18})$aryl group with n=1 to 4, m=0 to 3 and p=0 to 2, or a group $OR_x$, $SR_x$ or $NR_xR_y$ in which (i) $R_x$ and $R_y$, independently of each other, are chosen from a hydrogen atom and $(C_1-C_6)$alkyl, $(C_3-C_6)$cycloalkyl, $(C_6-C_{18})$aryl, $(C_6-C_{18})$aryl$(C_1-C_4)$alkyl, $(C_1-C_{12})$alkyl$(C_6-C_{18})$aryl, $(C_3-C_6)$cyclo-alkyl$(C_6-C_{12})$aryl, $(C_5-C_{12})$heteroaryl containing 1 to 3 heteroatoms, NR'R" and NHCOR'R" groups, R' and R", independently of each other, being chosen from a hydrogen atom and $(C_1-C_6)$alkyl, $(C_3-C_6)$cycloalkyl and $(C_6-C_{12})$aryl groups, and aromatic or non-aromatic $(C_5-C_{12})$ heterocycles, containing 1 to 3 heteroatoms, or (ii) $R_x$ and $R_y$ together form a linear or branched hydrocarbon-based chain containing from 2 to 6 carbon atoms, optionally comprising one or more double bonds and/or optionally interrupted with an oxygen, sulfur or nitrogen atom.

More specifically, R4 and R5 may correspond to a phenylpropanyl alcohol, fused with the general structure (I) in order to give rise to a flavonolignan.

The invention thus relates to their use in a composition, as an agent for pigmenting the skin and/or body hair and/or head hair, or as a hair loss counteractant. They may thus be dermatological or cosmetic compositions comprising as active agent at least one compound of general structure (I) or a derivative or analogue thereof or alternatively at least one plant extract containing at least one compound of general structure (I), the said active agent possibly being advantageously combined in the composition with a vehicle that is compatible with and suitable for the chosen mode of administration.

St Mary thistle (Silybum marianum (L.) Gaertner) from the Asteracea family is a Mediterranean plant, which also grows in North America, South America and Australia, which is used in traditional pharmacopoeias, especially for combating various liver complaints.

Silymarin and/or one of the constituents thereof in pure form or as a mixture have antioxidant properties that are used in the treatment of various toxic complaints (especially as an anti-hepatotoxic agent) and for promoting cell regeneration.

Patent application WO 99/55326 discloses the use of silymarin for restoring the level of glutathione in mammalian cells.

EP 180 505 discloses the use of silymarin in cosmetic preparations for retarding ageing of the skin.

WO 01/13879 discloses the cosmetic use of Silybum marianum oils for promoting the cutaneous absorption of compositions also comprising cynarin with a free-radical effect.

Carcinogenesis, Vol. 25, No. 8, 1459-1465, 2004, also discloses the use of silybin for protecting the skin against damage caused by UV radiation.

The present invention thus concerns the use of silymarin, or of one of the main constituents thereof alone or as a mixture, chosen from silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin or isolated enantiomers thereof and also salts thereof, for the manufacture of compositions for inducing, restoring or stimulating pigmentation of the skin, body hair or head hair.

The present invention also relates to the use of silymarin, or one of the main constituents thereof alone or as a mixture, chosen from silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin or isolated enantiomers thereof and also salts thereof, for the manufacture of compositions for preserving the integrity of the hair, for limiting its loss and for stimulating hair regrowth.

In one embodiment, the silymarin constituent is enantiomerically pure silybin or isosilybin. In this embodiment, the constituents are chosen from silybin A, silybin B, isosilybin A and isosilybin B, or salts thereof, or as a mixture.

According to one embodiment, silymarin or one of the constituents thereof alone or as a mixture is obtained by extraction of a plant of the genus *Silybum*.

According to one embodiment, silymarin or one of the constituents thereof alone or as a mixture is obtained by semi-synthesis or synthesis.

The compositions will be dermatological or cosmetic compositions comprising as active agent silymarin, or one of the main constituents thereof alone or as a mixture, chosen from silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin, and also salts thereof, the said active agent possibly being advantageously combined in the composition with a vehicle that is compatible with and suitable for the chosen mode of administration.

When the active agent is obtained by extraction, the production of a *Silybum* extract is most particularly intended. It is more especially an extract of *Silybum* cells and most specifically an extract of cells of at least one plant of the genus *Silybum* of the Asteracea family. This cell material may be obtained by in vitro or in vivo culturing. The term "in vitro culturing" means any technique known to those skilled in the art for artificially obtaining a plant or part of a plant. The term "in vivo culturing" means any culture technique for obtaining a plant or part of a plant. Thus, the extract may be an extract of an organ (root, stem, leaf or bark), or of organ cells, of at least one plant of the genus *Silybum* of the Asteracea family, or alternatively an extract of undifferentiated cells of at least one such plant. These extracts are enriched in flavonolignans in variable proportions depending on the type of extract. These purified extracts thus have the advantage of being free of any problem of toxicity compared with the crude extract. More particularly, three extraction/purification formulae may be envisaged: (i) a total extract of the plant, (ii) an extract intended for concentrating the taxifolin-based flavonolignans, and finally (iii) the production of taxifolin and pure derivatives.

Any extraction or purification method known to those skilled in the art may be used according to the invention. Mention may be made in particular of alcoholic (especially methanolic or ethanolic) or aqueous extracts or extracts using solvents such as ketones, esters, ethers, polyols or chlorinated solvents, and mixtures of at least two of the abovementioned solvents, for instance aqueous-alcoholic extracts.

A compound that is particularly suitable for use in the present invention is 2,3-dihydro-3-(4-hydroxy-3-methoxyphenyl)-2-(hydroxymethyl)-6-(3,5,7-trihydroxy-4-oxo-benzopyran-2-yl)benzodioxine or silybin, which may be used, however, as a mixture in the complex known as silymarin or else purified, or else may even be enantiomerically pure (use of only one isomer).

This compound has the advantage of being already used therapeutically as a hepato-protective agent. Numerous data concerning its harmlessness are already known and available. Furthermore, its industrialization is also already operational and inexpensive.

The main constituents of silymarin, alone or as a mixture, chosen from silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin and also salts thereof, may be obtained by a person skilled in the art via synthesis according to usual methods.

The present invention also relates to the cosmetic use of silymarin, or one of the main constituents thereof alone or as a mixture, chosen from silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin and salts thereof, in a composition, as an agent for tanning the skin and for maintaining, inducing and/or restoring the pigmentation of the hair, and/or as a hair-protecting agent and/or as a hair-loss counteractant and/or as a hair regrowth stimulant.

The invention also relates to the use of silymarin, or one of the main constituents thereof alone or as a mixture, chosen from silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin and salts thereof, for the manufacture of a topical or systemic dermatological composition for pigmenting the skin and/or body hair and/or head hair via a natural biosynthetic process, and/or as a hair-protecting agent and/or as a hair-loss counteractant and/or as a hair regrowth stimulant.

For cosmetic and dermatological use, the compositions of the invention may be in the form of creams, gels, lotions, milks, O/W and W/O emulsions, solutions, ointments, sprays, body oils, hair lotions, shampoos, after-shave lotions, soaps, lip-protecting sticks and makeup sticks and pencils.

In gel form, they comprise suitable excipients such as cellulose esters or other gelling agents, such as carbopol or guar gum.

These cosmetic and dermatological compositions may also be in the form of a lotion or solution in which the extracts and/or molecules are in encapsulated form, for example in microspheres. These microspheres may consist, for example, of fatty substances, agar and water. The active agents may also be incorporated into vectors such as liposomes, glycospheres, cyclodextrins, into chylomicrons, macro-, micro- or nanoparticles and also macro-, micro- and nanocapsules, and may also be adsorbed onto pulverulent organic polymers, talcs, bentonites and other mineral supports. These emulsions show good stability and may be kept for the time required for use at temperatures of between 0 and 50° C. without any sedimentation of the constituents or phase separation taking place.

The cosmetic compositions of the invention comprise from about 0.01% to 10% by weight and preferentially between 0.1% and 2.5% of active agents when they are in powder form and from about 0.01% to 2.5% and preferentially between 0.5% and 10% when they are in encapsulated form.

For the preparation of these compositions, silymarin, or one of the main constituents thereof alone or as a mixture chosen from silybin, (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin, and also salts thereof or a plant extract, are mixed with the excipients generally used in cosmetics.

The cosmetic compositions of the invention may also contain additives or adjuvants that are common in cosmetology, for instance antibacterial agents or fragrances, but also extracted and/or synthetic lipids, gelling and viscosity-increasing polymers, surfactants and emulsifiers, water-soluble or liposoluble active principles, plant extracts, tissue extracts, marine extracts or synthetic active agents.

The cosmetic compositions of the present invention may also comprise other additional active principles chosen for their action, for example for antisun protection, the antiwrinkle effect, the free-radical-scavenging and antioxidant activity, the anti-irritant activity, cell nutrition, cell respiration, cell hydration and regeneration, anti-seborrhoeic treatments, and also other active principles with action on skin tonicity or hair protection.

The cosmetic compositions of the present invention are preferably to be used daily by applying them one or more times a day.

The cosmetic compositions of the present invention are very well tolerated, show no phototoxicity and their application to the skin, for prolonged periods of time, involves no systemic effect.

alkaline extraction, relative to 100% of the control (the control corresponds to the test performed without test compound);

after culturing for 3 days under standard conditions:

the effects on the proliferation of normal human melanocytes by incorporation of tritiated thymidine into DNA (labelling for the last 24 hours), the effects on the metabolism of normal human melanocytes by incorporation of tritiated leucine into neosynthesized proteins (labelling for the last 24 hours).

The results are collated in the following tables:

Melanin Synthesis by Normal Human Melanocytes:

| Treatment | Concentration | Melanin (µg/ml) | sd | n | % | p | Proteins (mg/ml) | MTT (%) |
|---|---|---|---|---|---|---|---|---|
| Control | — | 27.7 | 0.38 | 3 | 100 | — | 0.645 | 100 |
| Silybin | 0.001% | 41.5 | 0.18 | 3 | 150 | P < 0.01 | 0.830 | 128 |
|  | 0.0002% | 37.1 | 0.97 | 3 | 134 | P < 0.01 | 0.792 | 126 |
|  | 0.00004% | 31.9 | 0.68 | 3 | 115 | P < 0.01 | 0.765 | 113 |

Oral application may also be envisaged. It is thus also worthwhile discussing compositions comprising at least silymarin, or one of the main constituents thereof alone or as a mixture, chosen from silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isosilybin, silydianin, silychristin, silandrin, silymonin and taxifolin and also salts thereof, combined with a pharmaceutically, cosmetically and dermatologically acceptable vehicle or excipient.

The dermocosmetic compositions are in the form of liquid, powder, paste or emulsion, alone or in combination with other substances. They comprise from about 0.01% to 25% by weight of flavonolignans, and more particularly of silybin, of the biosynthetic precursor thereof, taxifolin and derivatives, of silychristin or of a plant extract containing them.

For preparations of these dermocosmetic compositions, the extracts and/or pure compounds mentioned above, alone or as a mixture and/or in the form of salts, are mixed with excipients.

EXAMPLES

The examples that follow illustrate the invention without limiting its scope.

Example 1

Demonstration of the Activity on Melanogenesis in Melanocyte Cultures

A biological test demonstrated the stimulatory activity of silybin on melanin synthesis.

The melanogenesis-stimulating effect of silybin was measured on normal human melanocyte cultures.

For silybin, the following were determined:

after culturing for 10 days under standard conditions, in 24-well plates, in Promocell medium free of "phorbol myristate acetate" (PMA):

the cytotoxicity, by estimating the reduction of "methyl thiazolyl tetrazolium" (MTT), the amount of proteins, by assay according to the Bradford method and observation of the cell lawns, the amount of melanin present in the cultures, by spectrophotometric measurement of the melanin produced, after In all cases: concentrations in % (w/v); sd: standard deviation; p: statistical significance.

Effects on the proliferation and on protein neosynthesis of normal human melanocytes:

| Treatment | Concentration | cpm | sd | n | % | p |
|---|---|---|---|---|---|---|
| Proliferation (3H-thymidine), normal human melanocytes | | | | | | |
| Control | — | 6805 | 0 | 3 | 100 | — |
| Silybin | 0.001% | 3622 | 750 | 6 | 53 | P < 0.01 |
|  | 0.0002% | 5638 | 1104 | 6 | 83 | P > 0.05 |
| Protein synthesis (3H-leucine), normal human melanocytes | | | | | | |
| Control | — | 9751 | 993 | 12 | 100 | — |
| Silybin | 0.001% | 12099 | 1995 | 6 | 124 | P < 0.01 |
|  | 0.0002% | 11705 | 486 | 6 | 120 | P < 0.05 | cpm: counts per minute.

Silybin thus caused a significant increase in melanin production in the treated human melanocyte cultures. This stimulation is accompanied by an apparent moderate increase in melanocyte metabolism (MTT, proteins). This effect is not due to an increase in melanocyte proliferation (incorporation of thymidine), on the contrary, under these artificial conditions, the product has a tendency to limit proliferation, without any cytotoxic activity. Moreover, stimulation of the metabolic activity over shorter tests (protein neosynthesis over 72 hours) confirms a very weak stimulatory effect on melanocyte metabolism (protein synthesis increased by only 20%).

The product did not otherwise show any effect on the proliferation/protein synthesis of keratinocytes.

The melanogenesis-stimulating effect of silybin was measured on B16F10-line mouse melanoma cells.

For silybin, the following were determined:

after culturing for 7 days under standard conditions, in 24-well plates, DMEM medium containing 10% calf serum:

the cytotoxicity, by estimating the hydrolysis of MTT, the amount of proteins, by assay according to the Bradford method and observation of the cell lawns, the amount of melanin present in the cultures, by spectrophotometric measurement of the melanin produced, after alkaline extraction, relative to 100% of the control (the control corresponds to the test performed without test compound).

The results are collated in the following table:

| | | Melanin synthesis by B16F10-line melanocytes: | | | | | | |
|---|---|---|---|---|---|---|---|---|
| Treatment | Concentration | Melanin (μg/ml) | sd | n | % | p | Proteins (mg/ml) | MTT (%) |
| Control | — | 13.0 | 0.31 | 3 | 100 | — | 1.565 | 100 |
| Silybin | 0.001% | 33.0 | 0.83 | 3 | 254 | P < 0.01 | 1.457 | 89 |
| | 0.0002% | 15.0 | 0.35 | 3 | 115 | P < 0.01 | 1.594 | 100 |
| | 0.00004% | 13.0 | 0.58 | 3 | 100 | P > 0.05 | 1.553 | 100 |

Silybin thus caused a very marked increase in melanin production in the B16F10-line melanocyte cultures (250% of the control at 0.001%), which confirms the observed pro-pigmenting effect, on a second cell model. In this case, the stimulation is observed without modification of the cell metabolism, according to MTT and protein synthesis parameters, which confirms the specificity of the stimulation of melanin synthesis.

The binding of silybin to the receptor MC1-R (melanocortin-1 receptor) was studied. Structural data suggested a possibility of binding of these compounds to the receptor MC1-R (melanocortin-1 receptor), which is strongly involved in melanogenesis.

Silybin was tested in a test of displacement of an extremely powerful MC1-R ligand: displacement of [$^{125}$I]NDP-alpha-MSH, (according to Siegrist et al, 1988, J. Recept. Res., 8: 323-343).

The ligand has an affinity of the order of $10^{-10}$ M. At concentrations of 100 μM (0.005%) and higher, silybin significantly displaces this ligand (10% at 100 μM; 30% at 500 μM; higher concentrations were not tested, for reasons of solubility), indicating a specific impact on the receptor MC1-R. An effect of these compounds on the inhibition of phosphodiesterases, especially of type 4: increased cAMP, should also be noted.

Example 2

Demonstration of the Activity on Melanocyte Dendricity

The aim of this test is to show the effect of the compounds used according to the invention on the morphological modulation of melanocytes.

Method: Normal human melanocytes are treated at the time of inoculation with the compounds according to the invention for 2 days, under the conditions of the melanogenesis tests on human melanocytes, and then labelled with CFDA (carboxyfluorescein succinimidyl ester diacetate) and observed by fluorescence microscopy (green colouration).

Observations: see FIG. 1.

Results: In the absence of the compounds according to the invention, the melanocytes in culture are sparingly dendritic, or even bipolar. In the presence of the compounds according to the invention, the melanocytes show markedly greater dendricity.

Example 3

Demonstration of the Phagocytosis Activity of Keratinocytes

The aim of this test is to show the effect of the compounds used according to the invention on modulation of the phagocytosis of particles by the keratinocytes.

Method: Normal human keratinocytes are cultured in KSFM medium and treated for 24 hours with the compounds according to the invention, in the presence of calibrated fluorescent beads (Molecular Probes) of the size of melanosomes. The phagocytosis of the particles is visualized by fluorescence microscopy, and the cells are then harvested after trypsination and analysed by flow cytometry, to determine the number of cells that have phagocytozed a threshold number of particles and the intensity of the phagocytozed overall fluorescence (10 000 cells analysed per condition, in triplicate).

Figure 2:
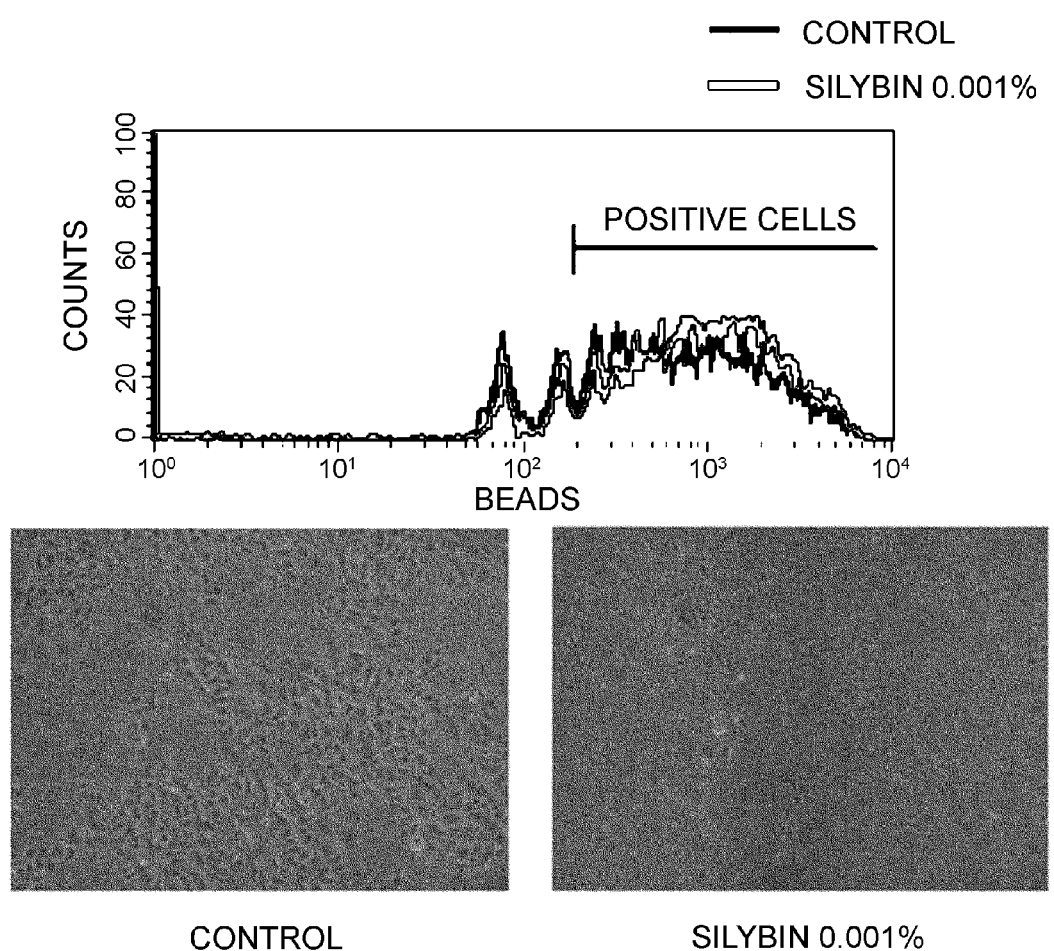
FIG. 2 shows flow cytometry analysis and fluorescence microscopy of normal human keratinocytes that are cultured in KSFM medium and treated for 24 hours with a compound containing 0.001% concentration silybin in the presence of calibrated fluorescent beads (molecular probes) of the size of melanosomes.

Observations: The effects of silybin are reported in the following table and FIG. 2:

| Treatment | Concentration | % Positive cells* | Mean | SD | % Control | p |
|---|---|---|---|---|---|---|
| Control | — | 35.39 | 36 | 2 | 100 | — |
| | | 33.8 | | | | |
| | | 38.02 | | | | |
| Silybin | 0.001% | 52.19 | 51 | 1 | 143 | p < 0.01 |
| | | 50.74 | | | | |
| | | 49.94 | | | | |
| | 0.0002% | 45.88 | 44 | 1 | 124 | p < 0.01 |
| | | 44.29 | | | | |
| | | 42.92 | | | | |

*cells which have phagocytozed more than twice the basal phagocytosis

Results: Silybin induces a significant and reproducible stimulation of phagocytosis of fluorescent particles that may be likened to melanosomes; this dose-dependent stimulation was measured by flow cytometry and by direct observation of the cell lawns via fluorescence microscopy.

Example 4

Demonstration of the Pro-Pigmenting Activity on the Hair

The aim of this test is to show the effect of the compounds used according to the invention on melanin synthesis in the follicles and their pigmentation.

Method: Normal human hair follicles are isolated by microdissection of human scalp (lifting) and cultured individually in vitro, in 24-well plates, according to Philpott et al, 1990, J. Cell. Sci., 3: 463-471, with a minimum of 15 homogeneous pigmentation hairs per condition. The follicles are cultured for 7 days in the presence of the compounds according to the invention. The follicles are photographed on D0 and D7 and the pigmentation is evaluated visually.

Figure 3:
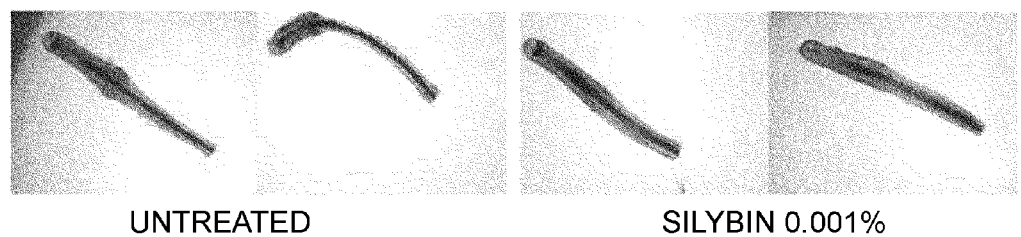
FIG. 3 shows photographs of normal human hair follicles that are isolated and cultured individually in vitro for 7 days in the presence of a compound containing 1.001% concentration silybin.
Figure 3:
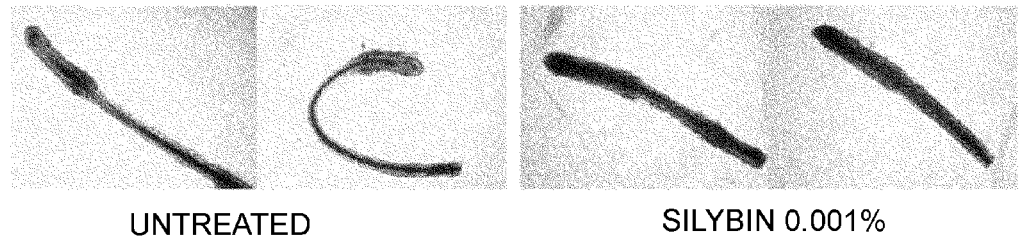
Figure 3:
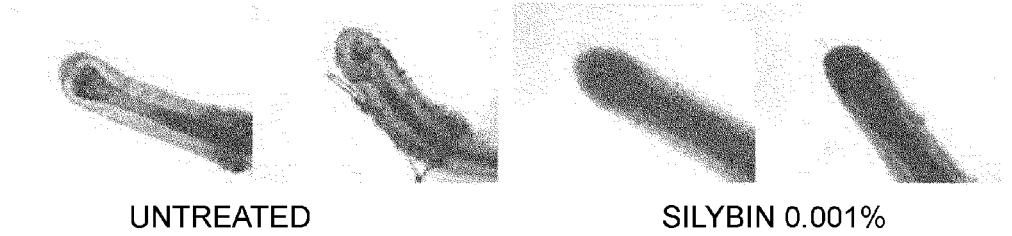

Observations: The effects of silybin are reported in FIG. 3.

Results: Silybin is not toxic to the hair and allows lengthening of the hair stem; it induces very marked pigmentation of the bulb and of the newly formed hair stem compared with untreated controls. The compounds used according to the invention thus stimulate melanin synthesis in the follicles and their pigmentation.

Example 5

Demonstration of Protection Against Degeneration of the Follicles (Hair Bulbs)

The aim of this test is to show the effect of the compounds used according to the invention on degeneration of the follicles in in vitro cultures of human hair follicles.

Method: Normal human hair follicles are isolated by microdissection of human scalp (lifting) and cultured as in Example 4. The bulbs are all precultured ("aged", without treatment) for 7 days (D7), and then left untreated or treated by the invention for a further 7 days (D14). The follicles are photographed and the morphology is analysed.

Figure 4:
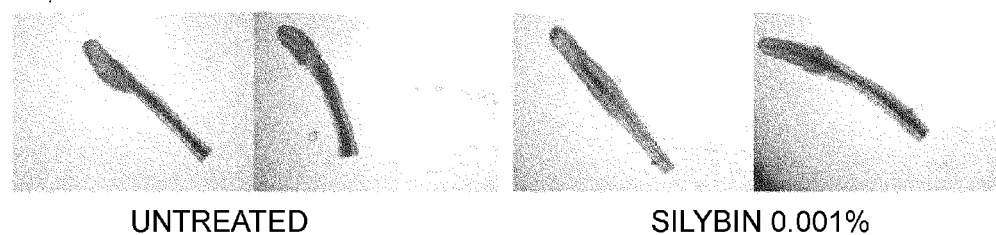
FIG. 4 shows photographs of normal human hair follicles that are isolated and cultured individually in vitro for 7 days in the presence of a compound containing 1.001% concentration silybin.
Figure 4:
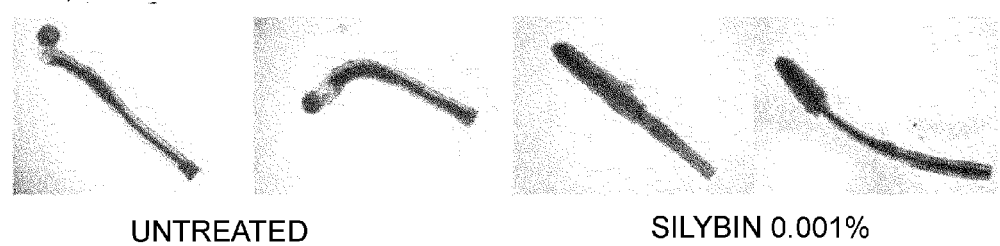
Figure 4:
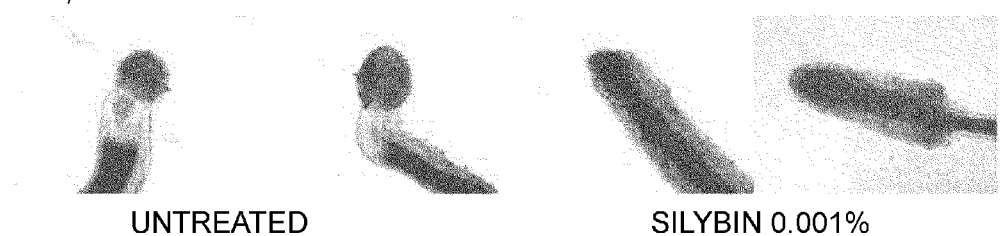

Observations: The effects of silybin are reported in FIG. 4.

Results: After culturing for 17 days, a majority of control follicles show signs of advanced degeneration, generally with a bulb in budding state. This follicular degeneration in culture is characterized by gradual budding of the bulb, followed by expulsion. The follicles treated with silybin have an apparently normal morphology, without visual budding of the bulb, and display pigmentation of all of the hair root.

Certain other taxifolin derivatives show activities analogous to those presented above. Mention is made, for example and in a non-limiting manner, of silydianin, rhodiolin, silyhermin, silandrin, hydnocarpin or silychristin.

The invention thus relates to the use of at least one compound of formula (I):

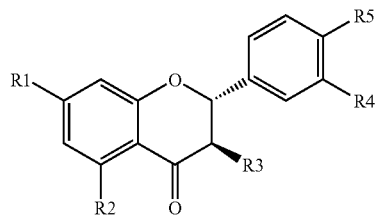

in which:
R1, R2, R3, R4 and R5, which may be identical or different, each represent
either a hydrogen atom,
or a halogen atom,
or a nitro, $(C_1-C_6)$alkyl, $(C_1-C_6)$alkylCOOH, $(C_1-C_6)$alkyl COONa, trifluoro$(C_1-C_6)$alkyl, $(C_3-C_6)$cycloalkyl, acyl, $(C_2-C_6)$alkenyl, $(C_2-C_6)$alkynyl, $(C_6-C_{18})$aryl, $(C_6-C_{18})$aryl-COOH, $(C_6-C_{18})$arylCOONa, $(C_6-C_{18})$aryl$(C_1-C_4)$alkyl, $(C_1-C_6)$alkyl$(C_6-C_{18})$aryl, $(C_5-C_{18})$heteroaryl containing from 1 to 3 heteroatoms, CH(OH)$(C_6-C_{18})$aryl, CO$(C_6-C_{18})$aryl, $(CH_2)_n$CONH—$(CH_2)_m$—$(C_6-C_{18})$aryl, $(CH_2)_n$SO$_2$NH—$(CH_2)_m$—$(C_6-C_{18})$aryl or $(CH_2)_n$CONH—CH (COOH)—$(CH_2)_p$—$(C_6-C_{18})$aryl group with n=1 to 4, m=0 to 3 and p=0 to 2,
or a group $OR_x$, $SR_x$ or $NR_xR_y$, in which (i) $R_x$ and $R_y$, independently of each other, are chosen from a hydrogen atom and $(C_1-C_6)$alkyl, $(C_3-C_6)$cycloalkyl, $(C_6-C_{18})$aryl, $(C_6-C_{18})$aryl$(C_1-C_4)$alkyl, $(C_1-C_{12})$alkyl$(C_6-C_{18})$aryl, $(C_3-C_6)$cycloalkyl$(C_6-C_{12})$aryl, $(C_5-C_{12})$heteroaryl containing 1 to 3 heteroatoms, NR'R" and NHCOR'R" groups, R' and R", independently of each other, being chosen from a hydrogen atom and $(C_1-C_6)$alkyl, $(C_3-C_6)$cycloalkyl and $(C_6-C_{12})$aryl groups, and aromatic or non-aromatic $(C_5-C_{12})$ heterocycles, containing 1 to 3 heteroatoms, or (ii) $R_x$ and $R_y$ together form a linear or branched hydrocarbon-based chain containing from 2 to 6 carbon atoms, optionally comprising one or more double bonds and/or optionally interrupted with an oxygen, sulfur or nitrogen atom, and more specifically, R4 and R5 may correspond to a phenylpropanyl alcohol, fused with the general structure (I) to give rise to a flavonolignan, in a cosmetic, pharmaceutical, especially dermatological or nutritional composition for inducing, restoring or stimulating pigmentation of the skin, body hair or head hair.

The invention also relates to the use of at least one pure isomer of silybin, a mixture of silybin isomers, a derivative or analogue thereof, silymarin or one of the constituents thereof such as silydianin, silychristin or isosilybin, or alternatively a plant extract containing them, especially of the genus *Silybum*, for inducing, restoring or stimulating pigmentation of the skin, body hair or head hair.

The invention relates to a composition comprising a compound as defined above, characterized in that the said derivative, which is synthetic or a plant extract, is capable of modulating the MC1R and PAR-2 activities simultaneously or independently of each other.

The invention relates to a cosmetic, dermatological, pharmaceutical or nutraceutical composition, characterized in that it comprises a pure silybin isomer, a mixture of silybin isomers, a derivative or analogue thereof, silymarin, or alternatively a plant extract containing it, especially of the genus *Silybum*.

The invention relates to the use of at least one compound or extract as defined above, in a cosmetic, pharmaceutical, especially dermatological or nutritional composition for protecting the skin or the hair from the harmful effects of exposure to sunlight, including light-induced ageing of the skin, skin inflammation and erythema, hair loss related to exposure to sunlight, skin cancers and photo-induced pathologies.

The invention relates to the use of at least one compound or extract as defined above, in a cosmetic, pharmaceutical, especially dermatological or nutritional composition for preserving the integrity of the hair, for limiting hair loss and for stimulating hair regrowth.

The invention relates to the use of at least one compound or extract as defined above, in a cosmetic, pharmaceutical, especially dermatological or nutritional composition for inducing, restoring or stimulating pigmentation of the skin, body hair or head hair.

The invention relates to a cosmetic, pharmaceutical or dermatological, topical or systemic composition as defined above, characterized in that it is combined with one or more other active agents that reinforce the desired main effect or that induce a complementarity of effects.

The invention relates to the use of lignans, especially of flavonolignans, for inducing, restoring or stimulating pigmentation of the skin, body hair or head hair.

The present invention relates to a pharmaceutical, dermatological or cosmetic composition comprising as active agent at least one taxifolin derivative or at least one plant extract containing at least one taxifolin derivative, for inducing, restoring or stimulating pigmentation of the skin, body hair or head hair, or for slowing down hair loss. Advantageously, the active agent(s) will be flavonolignans derived from silymarin and more specifically from silybin.

The invention claimed is:

1. A method of inducing or stimulating pigmentation of skin in a subject in need of such inducing or stimulating, the method comprising administering to the subject silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isolated enantiomers thereof and/or salts thereof to induce or stimulate the pigmentation of skin in the subject.

2. The method of claim 1, wherein the silybin is obtained by extraction of a plant of the genus *Silybum*.

3. The method of claim 1, wherein the silybin is obtained by semi-synthesis or synthesis.

4. The method of claim 1, wherein the silybin is enantiomerically pure.

5. The method of claim 1, wherein the administration is in a composition comprising from about 0.01% to 10% by weight of silybin.

6. The method of claim 5, wherein the composition comprises from about 0.1% to 2.5% by weight of silybin.

7. The method of claim 5, wherein the composition comprises from about 0.01% to 2.5% by weight of silybin.

8. A method of restoring pigmentation of skin in a subject suffering from hypopigmentation, the method comprising administering to the subject silybin (or 2,3-dihydro-3-(4-hydroxy-3-methoxyphenyl)-2-(hydroxymethyl)-6-(3,5,7-trihydroxy-4-oxobenzopyran-2-yl)benzodioxine), isolated enantiomers thereof and/or salts thereof to restore the pigmentation of skin in the subject.

* * * * *